US010226186B2

(12) United States Patent
Whitt et al.

(10) Patent No.: US 10,226,186 B2
(45) Date of Patent: *Mar. 12, 2019

(54) METHOD AND DEVICE FOR DETECTING AND ASSESSING REACTIVE HYPEREMIA USING SEGMENTAL PLETHYSMOGRAPHY

(71) Applicant: CORDEX SYSTEMS, INC, Annapolis, MD (US)

(72) Inventors: Michael David Whitt, South Bend, IN (US); Kathy Elizabeth Magliato, Pacific Palisades, CA (US); Stephen Ritterbush, Great Falls, VA (US); Thomas Justin Shaw, Reston, VA (US)

(73) Assignee: CORDEX SYSTEMS, INC., Annapolis, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/699,839

(22) Filed: Sep. 8, 2017

(65) Prior Publication Data

US 2018/0042489 A1 Feb. 15, 2018

Related U.S. Application Data

(63) Continuation of application No. 14/204,736, filed on Mar. 11, 2014, now Pat. No. 9,788,733, which is a
(Continued)

(51) Int. Cl.
*A61B 5/02* (2006.01)
*A61B 5/022* (2006.01)
(Continued)

(52) U.S. Cl.
CPC .......... *A61B 5/02007* (2013.01); *A61B 5/022* (2013.01); *A61B 5/0295* (2013.01);
(Continued)

(58) Field of Classification Search
CPC ............. A61B 5/02007; A61B 5/7239; A61B 5/02255; A61B 5/7282; A61B 5/022; A61B 5/0295; A61B 5/7275
See application file for complete search history.

(56) References Cited

U.S. PATENT DOCUMENTS 5,724,981 A 3/1998 Apple
6,309,359 B1 * 10/2001 Whitt .................... A61B 5/022
600/485

(Continued)

FOREIGN PATENT DOCUMENTS

| JP | 06319707 A | 11/1994 |
|---|---|---|
| JP | 2001087234 A | 4/2001 |
| WO | 2007/097654 A1 | 8/2007 |

OTHER PUBLICATIONS

International Search Report and Written Opinion issued in Application No. PCT/US2014/070803 dated Apr. 23, 2015.
(Continued)

*Primary Examiner* — Meredith Weare
(74) *Attorney, Agent, or Firm* — Katten Muchin Rosenman LLP

(57) ABSTRACT

A method for measuring reactive hyperemia in a subject is disclosed. The method includes performing a first segmental cuff plethysmography to generate a baseline arterial compliance curve and/or a baseline pressure-area (P-A) curve, performing a second segmental cuff plethysmography to generate a hyperemic arterial compliance curve and/or a hyperemic P-A curve, and calculating an area between the baseline and the hyperemic curves. The size of the area can be used as an indication of endothelial dysfunction (ED) and ED-related diseases.

18 Claims, 12 Drawing Sheets

Related U.S. Application Data continuation-in-part of application No. 12/792,504, filed on Jun. 2, 2010, now Pat. No. 8,708,921.

(60) Provisional application No. 61/213,369, filed on Jun. 2, 2009.

(51) Int. Cl.
*A61B 5/00* (2006.01)
*A61B 5/0295* (2006.01)
*A61B 5/0225* (2006.01)
*G06F 19/00* (2018.01)

(52) U.S. Cl.
CPC ........ *A61B 5/02255* (2013.01); *A61B 5/7239* (2013.01); *A61B 5/7275* (2013.01); *A61B 5/7282* (2013.01); *G06F 19/00* (2013.01)

(56) References Cited

U.S. PATENT DOCUMENTS

| | | | |
|---|---|---|---|
| 6,626,840 B2* | 9/2003 | Drzewiecki | A61B 5/02007 600/485 |
| 8,197,416 B1 | 6/2012 | Shankar | |
| 8,708,921 B2* | 4/2014 | Whitt | A61B 5/02007 600/481 |
| 9,788,733 B2* | 10/2017 | Whitt | A61B 5/02007 |
| 2002/0111554 A1* | 8/2002 | Drzewiecki | A61B 5/02007 600/490 |
| 2003/0065270 A1 | 4/2003 | Raines et al. | |
| 2004/0024324 A1 | 5/2004 | Bratteli | |
| 2004/0092832 A1 | 5/2004 | Schnall et al. | |
| 2005/0070805 A1 | 3/2005 | Dafni | |
| 2007/0021673 A1 | 1/2007 | Arbel et al. | |
| 2007/0225614 A1 | 9/2007 | Naghavi et al. | |
| 2009/0259131 A1 | 10/2009 | Tsuji et al. | |
| 2010/0298717 A1 | 11/2010 | Parfyonov et al. | |
| 2010/0305459 A1 | 12/2010 | Whitt et al. | |
| 2014/0276144 A1 | 9/2014 | Whitt | |
| 2018/0042490 A1* | 2/2018 | Whitt | A61B 5/02007 |

OTHER PUBLICATIONS

Liu, et al., "An Oscillometry-Based Approach for Measuring Blood Flow of Brachial Arteries," ICBME 2008, Proceedings 23, pp. 481-484, Feb. 11, 2009.

"Systolic vs. Diastolic Blood Pressure Range," Vaughn's Summaries, Dec. 17, 2008. http://web.archive.org/web/20081217003248/http://www.vaughns-1--pagers.com/medicine/blood-pressure.htm.

Wang, et al., "Efficacy of fenofibrate and simvastatin on endothelial function and inflammatory markers in patients with combined hyperlipidemia: relations with baseline lipid profiles," Atherosclerosis 170 (2003), pp. 315-323.

Rastaldo, et al., "Comparison between the effects of pentobarbital or ketamine/nitrous oxide anesthesia on metabolic and endothelial components of coronary reactive hyperemia," Life Sciences 69 (2001), pp. 729-738.

Philpott, et al., "Reactive Hyperemia and Cardiovascular Risk," Arteriosclerosis, Thrombosis, and Vascular Biology, 27 (2007), pp. 2065-2067.

Binggeli, et al., "Statins Enhance Postischemic Hyperemia in the Skin Circulation of Hypercholesterolemic Patients," Journal of the American College of Cardiology, vol. 42, No. 1, 2003, pp. 71-77.

Slides from Poster Presentation at the BMES Meeting (Biomedical Engineering Society Meeting); 1997.

File History of U.S. Appl. No. 12/792,504.

Notice of Reason for Refusal for Japanes Patent Application No. 2016-575299 dated Jul. 17, 2018.

Rajendran et al. "The Vascular Endothelium and Human Diseases." Int J Biol Sci. Nov. 9, 2013;9(10):1057-69.

Khan et al. "The Role of Endothelial Function and Its Assessment in Rheumatoid Arthritis." Nat Rev Rheumatol. 201 O May;6(5):253-61.

Filer et al. "Diffuse Endothelial Dysfunction is Common to ANCA Associated Systemic Vasculitis and Polyarteritis Nodosa." Ann Rheum Dis. Feb. 2003; 62(2): 162-167.

Zuliani et al. "Markers of Endothelial Dysfunction in Older Subjects with Late Onset Alzheimer's Disease or Vascular Dementia." J Neurol Sci. Sep. 15, 2008;272(1-2):164-70.

\* cited by examiner

METHOD AND DEVICE FOR DETECTING AND ASSESSING REACTIVE HYPEREMIA USING SEGMENTAL PLETHYSMOGRAPHY

RELATED APPLICATIONS

This application is a continuation application of U.S. patent application Ser. No. 14/204,736, filed on Mar. 11, 2014, which is a continuation-in-part application of U.S. patent application Ser. No. 12/792,504, filed on Jun. 2, 2010, which claims the priority of U.S. Provisional Patent Application No. 61/213,369, filed on Jun. 2, 2009. The entirety of all of the aforementioned applications is incorporated herein by reference.

FIELD

The technology relates generally to medical devices and diagnosis methods and, in particular, to methods and devices for measuring reactive hyperemia and endothelial dysfunction with segmental volume plethysmography and oscillometry.

BACKGROUND

Endothelial dysfunction (ED) has been shown to be of prognostic significance in predicting vascular events such as heart attack and stroke. It is the key event in the development of atherosclerosis and predates clinically evident vascular pathology by many years. ED can result from a variety of disease processes, such as hypertension, atherosclerosis, cardiovascular disease (heart disease and stroke), atrial fibrillation, congestive heart failure, peripheral vascular disease, septic shock, hypercholesterolemia, type I and II diabetes, erectile dysfunction, rheumatic arthritis, HIV, liver disease (cirrhosis, hepatitis B and C, non-alcoholic steatohepatitis, fatty liver disease), pre-eclampsia, heat stress, all forms of dementia and psychological illness, any and all illness related to localized or systemic inflammation, environmental factors such as smoking, ingestion of high glycemic index carbohydrates, sedentary lifestyle and obesity. ED is also associated with states of low grade, chronic inflammation with elevated C reactive protein which leads to atherosclerosis.

ED can be improved by risk factor modification: exercise, weight loss, cessation of smoking, the use of statin drugs, beta blockade, the treatment of hypertension and hypercholesterolemia, improved diet with reduction of trans fat intake, control of diabetes. Therefore, early detection of ED may allow not only early diagnosis and treatment of ED-related diseases, but also treatment of ED itself.

Plethysmography is a non-invasive technique for measuring the amount of blood flow present or passing through, an organ or other part of the body. Segmental volume plethysmography is performed by injecting a standard volume of air into a pneumatic cuff or cuffs placed at various levels along an extremity. Volume changes in the limb segment below the cuff are translated into pulsatile pressure that are detected by a transducer and then displayed as a pressure pulse contour. Segmental volume plethysmography has been commonly used to measure blood volume change. It may also be used to check for blood clots in the arms and legs.

SUMMARY

One aspect of the present application relates to a method for measuring reactive hyperemia in a subject. The method comprises the steps of performing a first segmental cuff plethysmography having an inflation phase and a deflation phase; generating a baseline arterial compliance curve and/or a baseline pressure-area (P-A) curve on a portion of the body of the subject, wherein the cuff pressure is increased to a first peak cuff pressure during the inflation phase and immediately reduced from the first peak cuff pressure during the deflation phase; performing a second segmental cuff plethysmography having an inflation phase, a holding phase, and a deflation phase; generating a hyperemic arterial compliance curve and/or a hyperemic P-A curve, wherein the cuff pressure is increased to a second peak level during the inflation phase, maintained at the second peak cuff pressure for a predetermined period of time during the holding phase, and then reduced from the second peak cuff pressure during the deflation phase; calculating the difference between the baseline arterial compliance curve and the hyperemic arterial compliance curve as an area between the arterial compliance curves, and/or the difference between the baseline P-A curve and the hyperemic P-A curve as an area between the P-A curves; measuring a level of reactive hyperemia based on the area between the arterial compliance curves and/or the area between the P-A curves, wherein a first cuff compliance curve is generated during the first segmental cuff plethysmography based only on data collected during the deflation phase of the first segmental cuff plethysmography and a second cuff compliance curve is generated during the second segmental cuff plethysmography based only on data collected during the deflation phase of the second segmental cuff plethysmography.

Another aspect of the present application relates to a method for determining endothelial dysfunction (ED) in a subject. The method comprises the steps of (a) inflating a cuff around a portion of the body of the subject and immediately deflating the cuff after reaching a first cuff pressure and measuring the volume and pressure changes in the cuff during the deflation process; (b) generating a first curve based on the measurements in step (a); (c) inflating the cuff around the portion of the body of the subject for the second time, maintaining the inflation at a second cuff pressure for a predetermined period of time, deflating the cuff, and measuring the volume and pressure changes in the cuff during the deflation process; (d) generating a second curve based on the measurements in step (c); (e) determining a difference between areas under the first curve and the second curve, wherein the first curve and the second curve are arterial compliance curves or pressure-area (P-A) curves; and (f) determining a level of endothelial dysfunction based on the difference determined in step (e), wherein a first cuff compliance curve is generated during step (a) and a second cuff compliance curve is generated during step (c) using a flowmeter to directly measure the volume change in the cuff, and a pressure sensor to measure pressure change for each known volume change, wherein the first curve is generated based the first cuff compliance curve, and wherein the second curve is generated based the second cuff compliance.

Another aspect of the present application relates to an apparatus for measuring reactive hyperemia in a subject. The apparatus comprises: an inflatable cuff having an inlet and an outlet; a pump connected to said inlet of said cuff for inflating the cuff; a flowmeter connected to said outlet of said cuff; a pressure transducer for measuring the pressure inside the cuff; and a computer configured to: generate a cuff compliance curve by directly measuring volume change in said cuff with said pump and pressure change inside the cuff with said pressure transducer; calculate an arterial compliance curve and a P-A curve during the inflation and deflation process of the cuff; and calculate difference between areas under a first arterial compliance curve and a second arterial compliance curve and difference between areas under a first pressure-area (P-A) curve and a second P-A curve.

BRIEF DESCRIPTION OF THE DRAWINGS

The detailed description will refer to the following drawings, wherein like numerals refer to like elements, and wherein.

DETAILED DESCRIPTION

Figure 1:
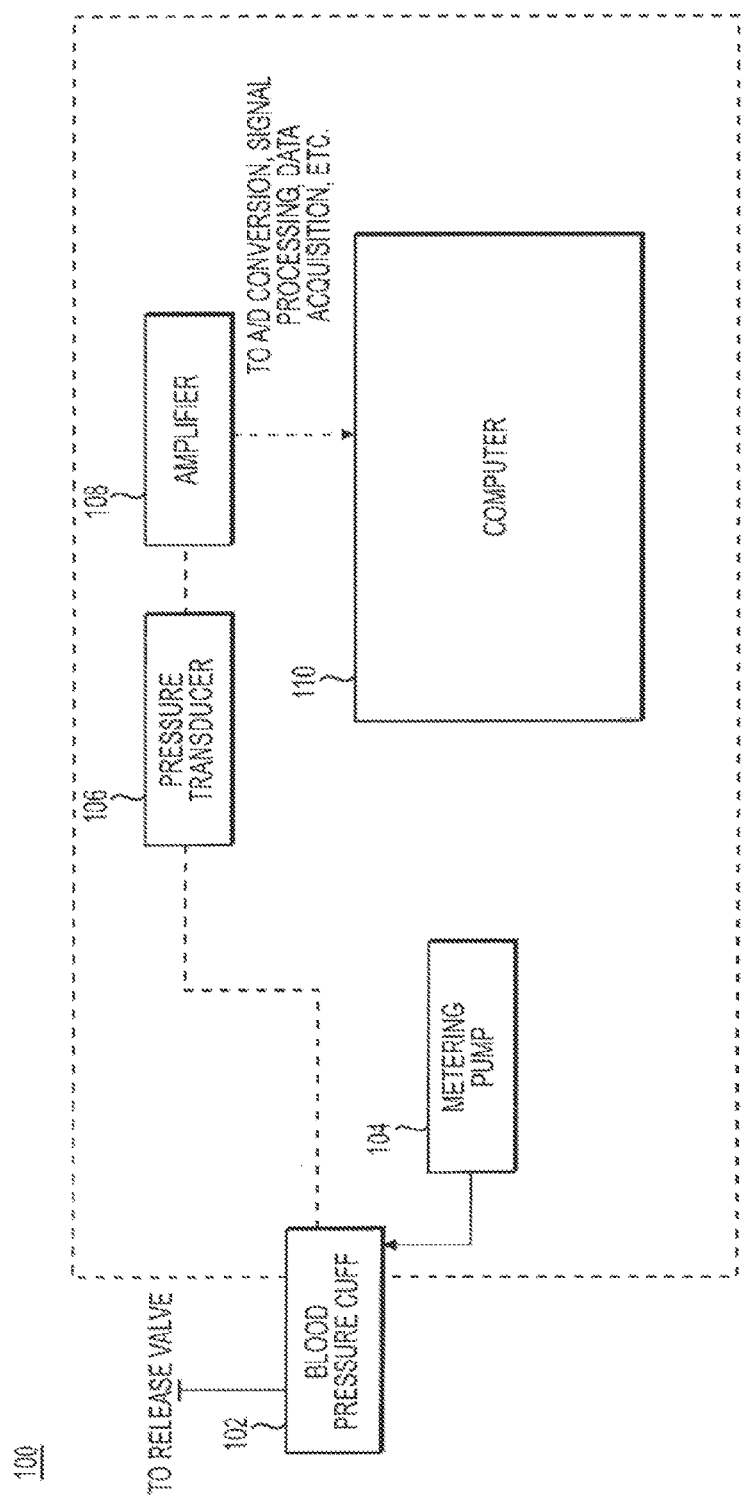
FIG. 1 is a block diagram illustrating an embodiment of a system for measuring arterial compliance, area and peripheral arterial flow.

Described herein are methods, systems and devices for measuring arterial compliance, and generating other measurements such as arterial volumetric blood flow waveforms and pressure-area curves, over the entire transmural pressure range. These measurements can be used to measure reactive hyperemia and detect, measure and monitor various ailments such as endothelial dysfunction, other cardiovascular diseases, and pre-eclampsia as well as for monitoring the effectiveness or efficacy of anesthesia.

Embodiments include a mathematical function-calibrated cuff plethysmography. A plethysmograph is an instrument for determining and registering variations in the size of an organ or limb resulting from changes in the amount of blood present or passing through it. The calibration is achieved with a process that combines a non-linear mathematical function and the output of a metering pump. Embodiments combine concepts of segmental volume plethysmography and oscillometry to provide an actual measurement of arterial compliance over the entire transmural pressure range. Segmental volume plethysmography is a technique that is performed by injecting a standard volume of air into a pneumatic cuff or cuffs placed at various levels along an extremity. Volume changes in the limb segment underneath the cuff are translated into pulsatile pressure that are detected by a transducer and then displayed as a pressure pulse contour. Oscillometry is a process that is used to measure changes in pulsations in arteries, especially arteries of the extremities. Embodiments also generate a pressure-area curve and arterial volumetric blood flow waveforms over the entire transmural pressure range. Transmural pressure is pressure across the wall of a cardiac chamber or the wall of a blood vessel. Transmural pressure is calculated as intracavity pressure (i.e., the pressure within the cardiac chamber or blood vessel) minus extracavity pressure (i.e., the pressure outside the cardiac chamber or blood vessel).

Embodiments are used to measure reactive hyperemia and endothelial dysfunction, which is an early measure of a functional abnormality in the endothelium. The endothelium is the inner most layer of the arterial wall and is made up of a thin layer of flat endothelial cells. Endothelial dysfunction, or ED, is a well established response to cardiovascular risk factors and precedes the development of atherosclerosis (which leads to plaque development). When ED occurs, the magnitude of nitric oxide secretion is reduced and arterial vasodilation is also reduced. These changes lead to reduced reactive hyperemia that can be measured using the method and devices described herein.

ED is a predictor of overall vascular health. Accordingly, ED is an early indicator of cardiovascular disease. Indeed, ED has been shown to significantly and directly correlate to cardiovascular events such as myocardial infarction, stroke, sudden death, and heart failure. By measuring the degree of ED, embodiments described herein can be highly predictive of cardiovascular events and disease. Clinically, ED can predict the occurrence of de novo type II diabetes and the progression of metabolic syndrome to type II diabetes. ED is also associated with peripheral vascular disease and chronic renal failure, and has been shown to predict pre-eclampsia in pregnant women. Pre-eclampsia is a serious medical condition developing in late pregnancy for which there is no known cure. Pre-eclampsia is characterized by high blood pressure and proteinuria (protein in the urine). Pre-eclampsia may lead to blindness, kidney failure, liver failure, placental abruption, convulsions, and HELLP syndrome (a triad of Hemolytic anemia, Elevated Liver enzymes, Low Platelets). Pre-eclampsia occurs in as many as 10% of all pregnancies and can be fatal to both mother and child. ED has been shown to be an early warning sign for pre-eclampsia.

Additionally, interventional studies have shown a regression of ED with the treatment of risk factors through diet, exercise, weight loss, smoking cessation, diabetic management, and drugs such as statins and various lipid lowering medications. Consequently, embodiments described herein may also be used as a means to monitor progress and guide treatment and therapy in patients with ED-related diseases such as cardiovascular disease.

For example, there are two distinct populations in which measuring endothelial dysfunction (ED) is both clinically valuable and efficacious. One population consists of asymptomatic patients at risk for cardiovascular disease (CVD). The other population is patients with known CVD who are on medical therapy. In patients at risk for CVD, measuring ED can serve as an early sign of progressive heart disease. In at-risk patients taking medications for known CVD, measuring ED can also monitor progress and guide treatment.

In one embodiment, methods and devices described herein are used to monitor progress and guide treatment and therapy in patients who are taking statins. Currently, physicians prescribe statins but have no established method for measuring their effect on decreasing ED, an important component of how statin therapy works. Using reactive hyperemia as an indicator of ED, the methods and devices described herein could be used to measure the efficacy of statin drugs as well as risk factor modification (i.e., weight loss, blood sugar control, smoking cessation etc) in improving ED. These methods involve measuring the reactive hyperemia and comparing the level of hyperemia in patients at different stages of the treatment. Where the efficacy of a medical treatment, such as statin treatment, is determined, the first measurement of reactive hyperemia is preferably a measurement taken prior to the initiation of the treatment, while the subsequent measurements are taken during the course of the statin treatment. The frequency of the measurement can be determined by the medical care provider. The medical care provider may further modify the treatment regimen based on the outcome the measurements.

The ability to measure accurate arterial flow waveforms using embodiments described herein may be beneficial in surgical, ambulatory and outpatient health care situations. Arterial flow waveform monitoring using embodiments described herein provides additional benefits beyond simple blood pressure monitoring. For example, a patient with hypovolemic shock would present the following physical manifestations in the earliest stage (referred to as the compensatory stage): increased heart rate, peripheral vasoconstriction and decreased cardiac output. An accurate arterial flow waveform measurement, such as provided by the embodiments described herein, can be obtained at any transmural pressure providing real-time, non-invasive measurement of cardiac output changes over time, in addition to constant accurate monitoring of heart rate and vascular tone.

Embodiments described herein measure ED and reactive hyperemia (an increase in the quantity of blood flow to a body part resulting from the restoration of its temporarily blocked blood flow). Some embodiments make these measurements by combining oscillometry and segmental volume plethysmography fundamentals and applying non-linear equations for cuff compliance. Cuff compliance is the amount of volume change that takes place with the given pressure change of a blood pressure cuff. This relationship has demonstrated a non-linear relationship in previous studies. However, the non-linear relationship varies from cuff to cuff as well as depending on how the cuff is placed on the limb. An earlier patent, U.S. Pat. No. 6,309,359 ("the '359 patent"), which is hereby incorporated by reference, also combined oscillometry and segmental volume plethysmography fundamentals to make non-invasive determinations of peripheral arterial lumen area. However, the method and apparatus described in the '359 patent do not apply or use a non-linear, mathematical equation to generate a cuff compliance curve, instead simply using the cuff pressure that most closely corresponds to actual cuff pressure. The '359 patent method and apparatus also use different equipment, including requiring a high-frequency pump that operates at a frequency that is significantly higher than the arterial cycle frequency, which is typically in the range of 25-35 Hz. Moreover, each point of data used by the '359 patent is obtained as the cuff pressure descends, as opposed to during inflation (pressure increasing) and deflation (pressure decreasing).

With reference now to FIG. 1, shown is a block diagram illustrating an embodiment of a system 100 for measuring arterial compliance. System 100 includes blood pressure cuff, meter, pump and hardware and/or software necessary for data acquisition described herein. Embodiment of system 100 includes a blood pressure cuff 102, metering pump 104, pressure transducer 106, amplifier 108 and computer 110. Blood pressure cuff 102 may be a standard blood pressure cuff 102 traditionally inflated to apply pressure to a limb so that blood pressure may be measured. The blood pressure cuff 102 is typically placed around the upper arm of the patient. However, the device could be used when placed around any portion of a limb for adults, children, or animals. Blood pressure cuff 102 size may be configured for the intended use in each case. Metering pump 104 includes a pump used to inflate blood pressure cuff 102 with a volume of air and a meter to measure inflation level of cuff (volume of air (e.g., in liters/minute) injected into the cuff 102). In one embodiment, the pump 104 is a low frequency pump. Pressure transducer 106 detects pulsatile pressure in the arteries of the limb by measuring the pressure in the cuff. The pressure transducer 106 generates a signal, indicative of the pulsatile pressure that is input into the amplifier 108. Amplifier 108 amplifies the pulsatile pressure signal and inputs the amplified signal into the computer 110.

The computer 110 may perform analog to digital (A/D) conversion of the amplified signal, as necessary, process the signal to acquire the necessary data, perform the methods, including calculating and applying the mathematical equations and generating the various curves, graphs and other displays, described herein. The computer 110 may be a general purpose computer with a processor(s) and memory that stores instructions (e.g., as one or more computer programs) to perform these functions, or a special purpose computer so programmed. Accordingly, the software included on the computer 110 may include one or more data acquisition and mathematical programs and is capable of developing the non-linear mathematical functions used in the method, performing band-pass filtering and other filtering and signal processing as necessary, and performing mathematical transformations, e.g., for area measurement under curves and numerical integration of arterial compliance curves for the development of pressure-area curves. Alternatively, instead of or in addition to computer 110, system 100 may include circuitry to perform some of these functions, include a separate A/D converter, a band-pass filter and other specialized circuitry.

Components of the system 100, such as the metering pump 104, pressure transducer 106, amplifier 108 and computer 110 may be housed within a single housing, as indicated by dashed lines in FIG. 1, connected to the blood pressure cuff 102.

Figure 3:
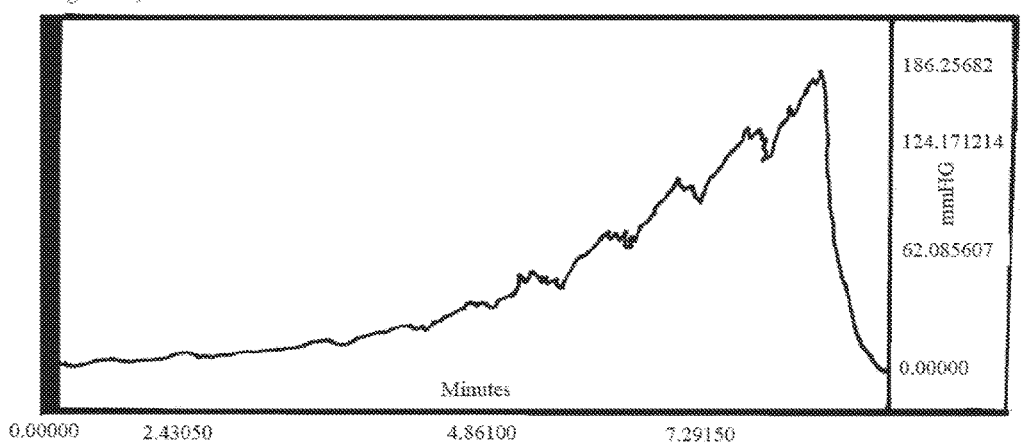
FIG. 3 is a graph illustrating data acquired using an embodiment of the system and method for measuring arterial compliance, area and peripheral arterial flow.

Embodiments of the method described herein obtain/acquire data during both inflation and deflation of the blood pressure cuff 102. In embodiments, a known volume of air is injected into the blood pressure cuff 102 at each increment from 0 mm Hg to a pressure significantly higher than the patient's systolic blood pressure (i.e., pressure that corresponds to the pressure in the arteries as the heart contracts and pumps blood into the arteries), yet not too uncomfortable for the patient (e.g., approximately 180 mm Hg). Each pressure change (dP) is measured for each known volume change (dV) along the entire pressure ascent. FIG. 3 is a chart of data acquired during the inflation process.

In some embodiments, the above-described data (measured pressure change for each known volume change) obtained during the inflation is used to develop $(dV/dP)_{cuff}$ versus average cuff pressure curve (referred to as "the average cuff pressure curve"), where dV is change in volume, dP is change in pressure and $(dV/dP)_{cuff}$ is cuff compliance, which changes non-linearly with cuff pressure.

The data obtained above is plotted on the average cuff pressure curve. A non-linear regression is performed on this data, developing an equation where $(dV/dP)_{cuff}$ can be obtained at any cuff pressure. In one embodiment, the non-linear regression is performed using inverse polynomial second order functions. Successful coefficients of determination have been developed using such functions. In some embodiments, data points are obtained during deflation where $Y=(dV/dP)_{cuff}$ and x equals mean cuff pressure. From these points a nonlinear regression inverse second order polynomial equation can be generated.

In other embodiments, during deflation of the blood pressure cuff (the descent portion of the average cuff pressure curve), various additional data is obtained and additional functions are performed. In one embodiment, band pass filtering method (i.e., band pass filtering at various frequencies filters out other data so as to determine desired pressure data) may be used to obtain systolic blood pressure, diastolic blood pressure, and mean arterial blood pressure (i.e., the average blood pressure during a single cardiac cycle (i.e., over one cycle of a given arterial pressure waveform)) via oscillometry. In another embodiment, band pass filtering is used to provide the magnitude of pressure pulses that take place at each cuff pressure $(dP)_{artery}$.

Arterial compliance $(dV/dP)_{artery}$, which provides the measure of arterial smooth muscle activity and resulting endothelial dysfunction) at any transmural pressure can then be obtained via the following equation:

$$\left(\frac{dV}{dP}\right)_{artery} = \frac{(dP)_{artery} \times \left(\frac{dV}{dP}\right)_{cuff}}{[\text{Systolic} - \text{Diastolic}]} \quad \text{Equation 1}$$

Arterial Compliance Calculation at Any Transmural Pressure

A curve is generated using Equation 1. The integration of the curve obtained from Equation 1 results in a pressure-area (P-A) curve. (Note: all volume measurements can be converted to area measurements if volume is divided by effective cuff length). All compliance measurements can be normalized by using Equation 2 below, where all volume measurements can be converted to area by once again dividing by effective cuff length.

$$C = \frac{(dV/dP)_{artery}}{V_0} \quad \text{Equation 2}$$

Normalized Arterial Compliance Equation $V_0$ is base volume of patient. By dividing the arterial compliance by the patient base volume, the arterial compliance is normalized. The process described above may be used to perform a variety of measurements.

Figure 14:
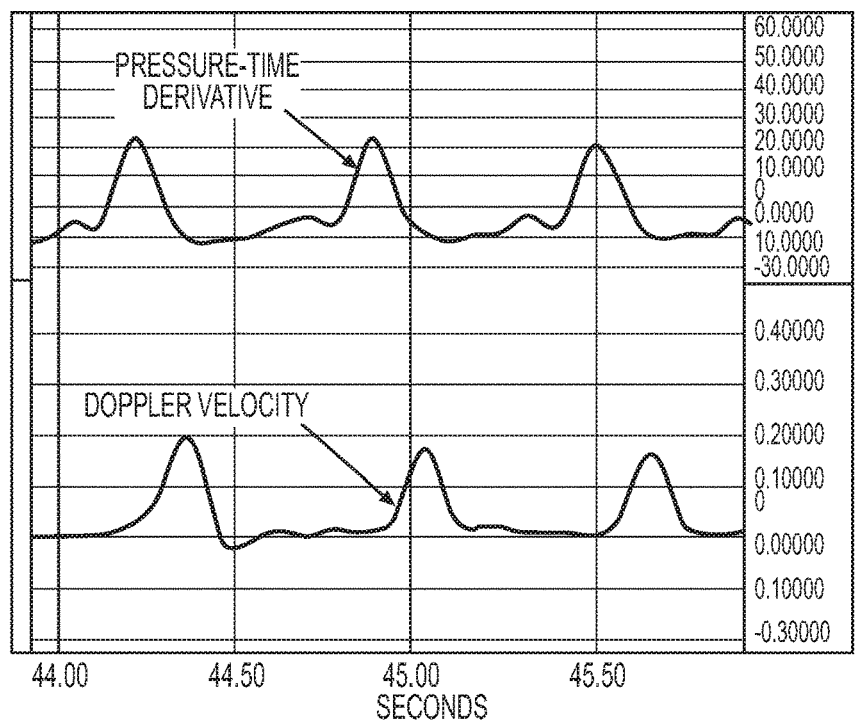
FIG. 14 shows exemplary pressure-time derivative and Doppler velocity waveforms.
Figure 15:
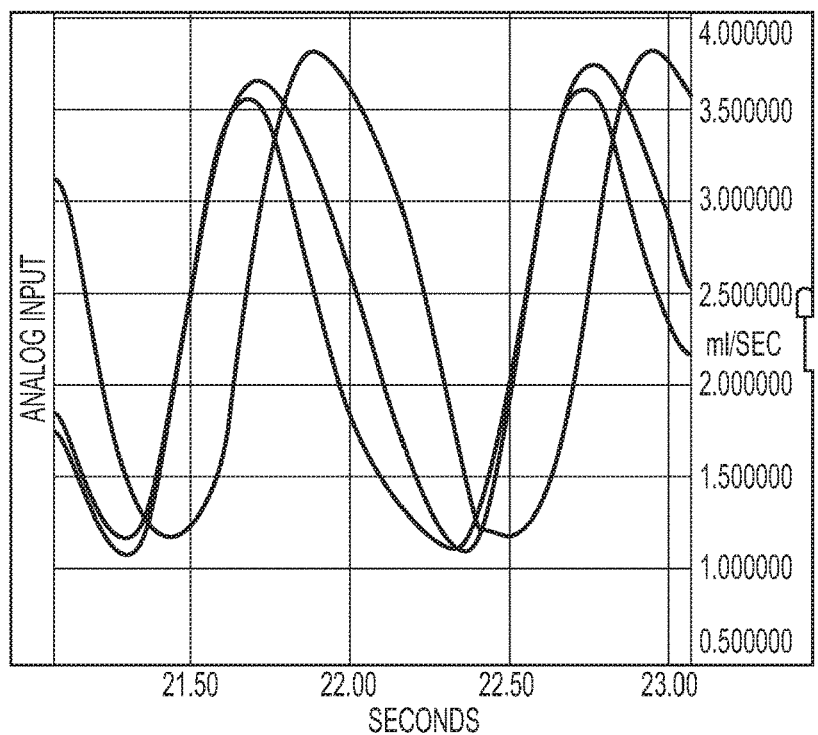
FIG. 15 shows exemplary flow waveforms calculated from pressure-time derivatives.

In one embodiment, the process is used for the development of an accurate arterial flow waveform by obtaining values for $(dV/dP)_{artery}$ at any transmural pressure, taking derivative of the original pressure descent waveform to obtain a waveform that is $(dP/dt)_{artery}$, and multiplying $(dP/dt)_{artery}$ by $(dV/dP)_{artery}$ to obtain an accurate flow waveform. The result is an accurate arterial flow waveform $(dV/dt)_{artery}$. FIG. 14 shows an exemplary pressure-time derivative and Doppler velocity waveforms and FIG. 15 shows exemplary flow waveforms calculated from pressure-time derivatives In another embodiment, the process is used for the measurement of endothelial dysfunction by obtaining a baseline arterial compliance curve and pressure-area curve as discussed above, holding the blood pressure cuff above a patient's systolic pressure for a given period of time (inducing hyperemia), obtain a second (i.e., hyperemic) compliance curve and pressure-area curve, and calculating the difference between the baseline curve and the hyperemic curve. The difference between the two curves represents the degree of endothelial dysfunction.

Figure 2:
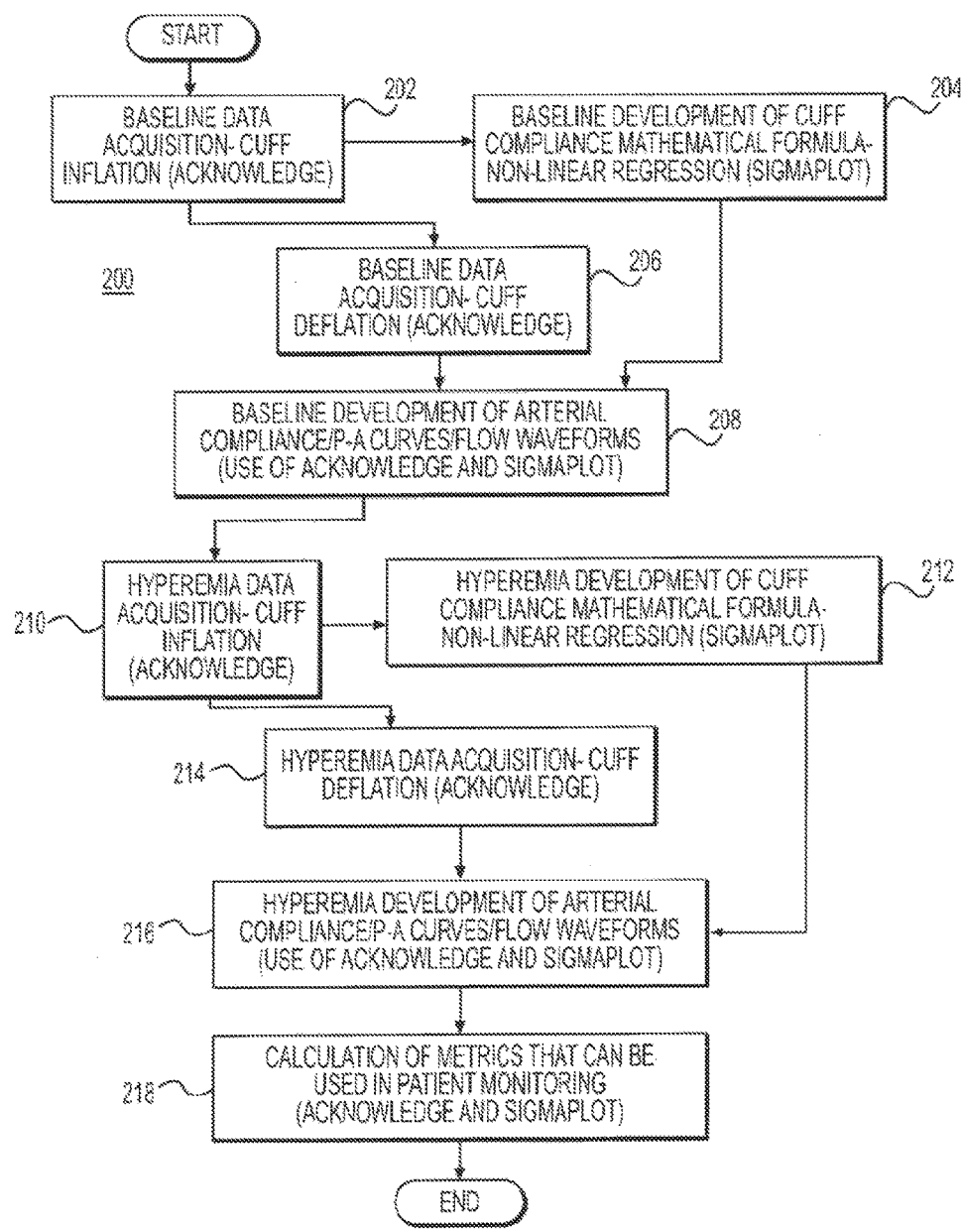
FIG. 2 is a flow chart illustrating an embodiment of a method for measuring arterial compliance, area and peripheral arterial flow

With reference now to FIG. 2, shown is a flowchart illustrating a method 200 for measuring arterial compliance. Baseline data is acquired during cuff inflation, block 202. See FIG. 3 for a graph of baseline data acquired during cuff inflation. The baseline data acquisition 202 may include using the metering pump 104 and pressure transducer 106 during cuff 102 inflation to measure air volume injection into the pump and cuff pressure, respectively. The baseline data acquisition 202 may further include placing the cuff 102 about a peripheral limb of a patient or subject and starting the cuff at 0 mm Hg. A known volume of air may be injected into the cuff 102 while recording cuff pressure change. The baseline data acquisition 202 may be accomplished, e.g., using data acquisition software program running on computer 110. The data acquisition program may receive input from pressure transducer 106 and/or metering pump 104 (e.g., that has been converted to digital via A/D converter and/or otherwise signal processed). A variety of data acquisition programs may be used, such as, for example, Acknowledge™. The baseline data acquisition 202 obtains the cuff compliance at given average cuff pressure, where average cuff pressure equals the cuff pressure after a known volume of air injection plus the cuff pressure before the known volume of air injection, divided by two (2). As described above, the volumetric inflation of the cuff is continued up to a pressure significantly higher than the subject systolic pressure yet not too uncomfortable for the subject (e.g., approximately 180 mm Hg).

Baseline cuff compliance equation/formula is generated, block 204. As indicated above, this may be achieved using non-linear regression. In embodiments, the baseline cuff compliance formula generation can begin as soon as cuff inflation has been completed. A mathematical equation representing cuff compliance may be developed by (i) plotting average cuff pressure (x) versus cuff compliance (y) and performing a non-linear regression as stated above. The baseline cuff compliance equation/formula may be generated 204 using a mathematical software program running on computer 110. The mathematical program may receive input from the data acquisition program and may perform, e.g., non-linear regression using, e.g., an inverse polynomial second order function(s). A variety of data acquisition programs may be used, such as, for example, SigmaPlot™.

With continued reference to FIG. 2, additional baseline data is acquired during cuff deflation as described above, block 206. Additional baseline data acquisition 206 may be performed, e.g., using data acquisition program. After this additional baseline data acquisition 206 is performed, band-pass filtering and development of arterial compliance curves, P-A curves and arterial flow waveforms are performed, block 208.

To develop baseline curves and waveforms, the pressure in the cuff is immediately released after the cuff pressure has gone above the patient systolic pressure and the measurements described above are taken. In other words, cuff pressure is raised so that it is above the patient systolic pressure and then immediately released. To develop reactive hyperemia curves and waveforms, the cuff pressure is held for a period of time sufficient to trigger an endothelial reaction and the measurements described above are taken. In embodiments described herein, the period of time is the time that is necessary to achieve total relaxation of the patient's smooth muscle tissue. Relaxation of the smooth muscle tissue is typically necessary to achieve accurate reactive hyperemic measurements. In one embodiment, the cuff pressure is held for a period of 1-10 minutes. In another embodiment, the cuff pressure is held for a period of 2-5 minutes. In yet another embodiment, the cuff pressure is held for about 5 minutes. The longer the cuff pressure can be held, the more assured the tester will be that the patient's smooth muscles have been relaxed and accurate reactive hyperemic measurements will be taken. The usual limiter on holding the cuff pressure is patient comfort; the longer the cuff pressure is held the more uncomfortable and, eventually, painful the procedure becomes. Elderly, ill or weakened patients tend to be able to withstand less time than younger, healthy patients.

After the baseline data has been generated, as described above, hyperemia data may be generated by basically repeating the above steps after a brief period of patient hyperemia. Hyperemia data is acquired during inflation of the cuff, block 210. The hyperemia data may be acquired by again starting the cuff at 0 mm Hg and inflating the cuff as described above. Acquisition 210 may include using the metering pump 104 and pressure transducer 106 during cuff 102 inflation to measure air volume injection into the pump and cuff pressure, respectively. Again, a known volume of air may be injected into the cuff 102 while recording cuff pressure change.

With continuing reference to FIG. 2, hyperemia cuff compliance mathematical equation is generated, block 212. Again, the hyperemia cuff compliance mathematical equation may be generated as described above. Additional hyperemia data is acquired during cuff deflation, block 214. After this additional data is acquired, band-pass filtering and development of arterial compliance curves, P-A curves and arterial flow waveforms for hyperemia are performed, block 216. Metrics to detect conditions or monitor the patient are calculated, block 218. The metrics may include, e.g., (a) comparing various curves of baseline data and hyperemic data, (b) calculating the differences between the curves as an area between the curves, and, e.g., (c) determining a level of ED (or, e.g., the presence of pre-eclampsia or other diseases, etc.) based on the calculated area. For example, such metrics may provide outputs indicating, for example, the presence of ED In one embodiment, the change between arterial compliance normal (baseline) curve, generated in 208, and the arterial compliance hyperemia curve, generated in 216, is calculated at a given transmural pressure.

In another embodiment, the change between arterial compliance normal (baseline) curve, generated in 208, and the arterial compliance hyperemia curve, generated in 216, can be calculated across a range of transmural pressures.

In another embodiment, the change between P-A normal (baseline) curve, generated in 208, and the P-A reactive hyperemia curve, generated at 216, is calculated at a given transmural pressure.

In another embodiment, the change between P-A normal (baseline) curve, generated in 208, and the P-A reactive hyperemia curve, generated at 216, is calculated across a range of transmural pressures.

In another embodiment, arterial flow waveforms (at any given transmural pressure or range of transmural pressures) for normal (baseline) curves and/or reactive hyperemia curves are calculated and compared.

In another embodiment, average flow waveforms (at any given transmural pressure or range of transmural pressures) for normal (baseline) curves and/or reactive hyperemia curves are calculated and compared.

In another embodiment, the computer 110 contains means for calculating an arterial compliance curve and a P-A curve during the inflation and deflation process of the cuff, means for calculating difference between areas under a first arterial compliance curve and a second arterial compliance curve and difference between areas under a first pressure-area (P-A) curve and a second P-A curve, and means for band pass filtering data.

Many of these metrics are significant in that they have never been performed over a range of transmural pressures. Other devices that perform similar metrics only do so for single points of data. Conducting these metrics over a range of transmural pressures allows more data to be compared and more information gathered from the results. The above metrics enable results to be compared over a range of pressures. More importantly, comparing the above curves of data enables the differences between the curves to be calculated as an area (see FIGS. 7-8). The lesser the area between the curves, the higher degree of ED; in other words, there is an inverse relationship between the area and the amount of ED. In certain embodiments, a scoring system is developed in which certain amounts of area (e.g., a range of area), calculated from the differences between the curves, correspond to certain levels of ED.

With reference to FIG. 3, shown is a graph of sample data acquisition during cuff inflation and deflation. The graph shows cuff pressure over time. By noting the time, the change in cuff pressure over a given time can be determined and compared to the change of cuff injection volume (not shown here) over the same time. Using this data, cuff compliance and average cuff pressure can be calculated.

Figure 4:
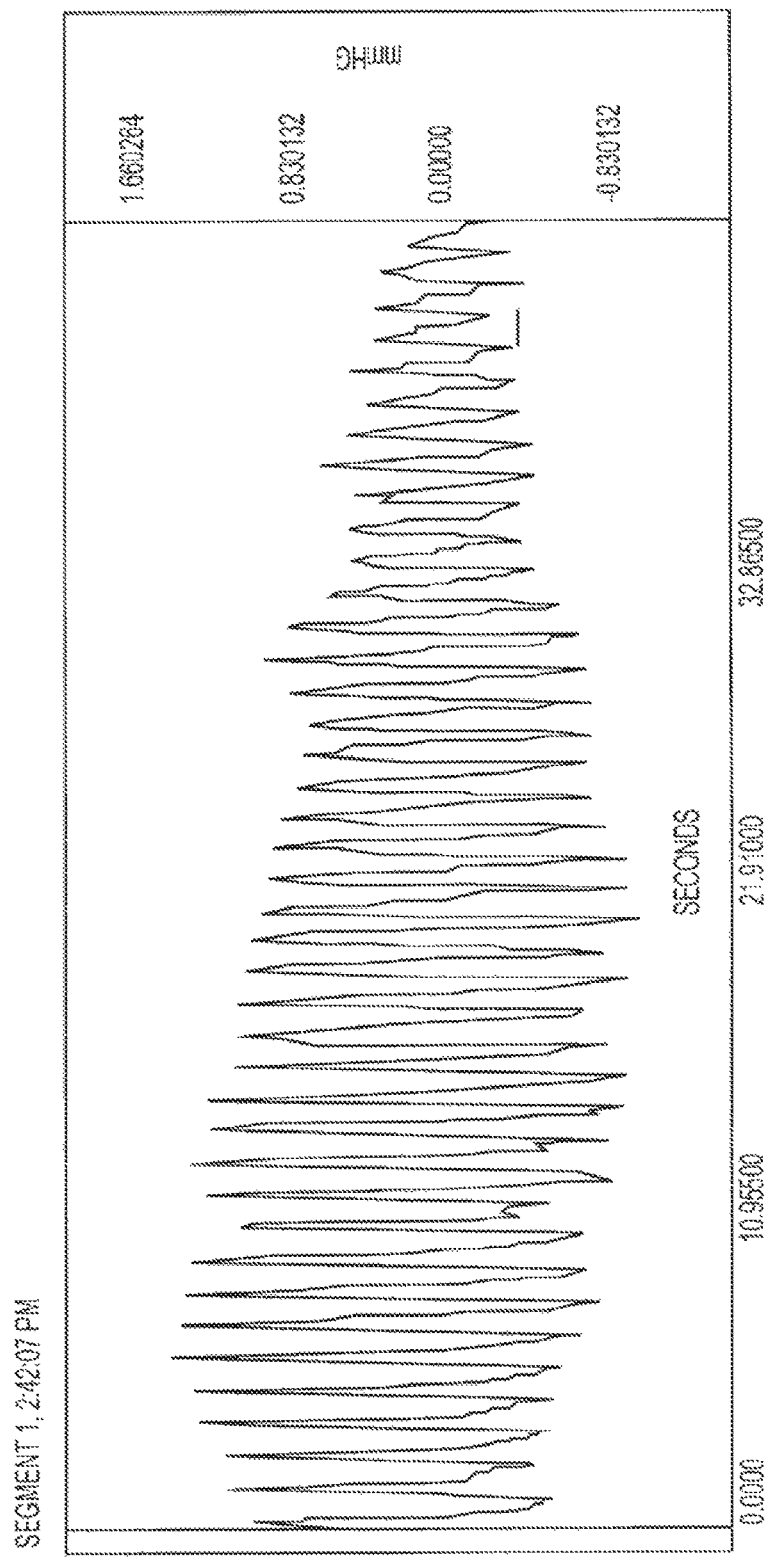
FIG. 4 is a graph illustrating data acquired and filtered using an embodiment of the system and method for measuring arterial compliance, area and peripheral arterial flow FIG. 5 includes graphs illustrating cuff compliance calculated using an embodiment of the system and method for measuring arterial compliance, area and peripheral arterial flow

With reference to FIG. 4, shown is a graph of sample data obtained during descent (deflation of cuff) that has been band pass filtered to provide arterial pressure pulses. The band pass filtering removes other pressure data received from the pressure transducer to leave only, in this example, the arterial pressure pulse data. In this example, the band pass filtering may be performed at 0.5 to 5.0 Hertz.

Figure 5:
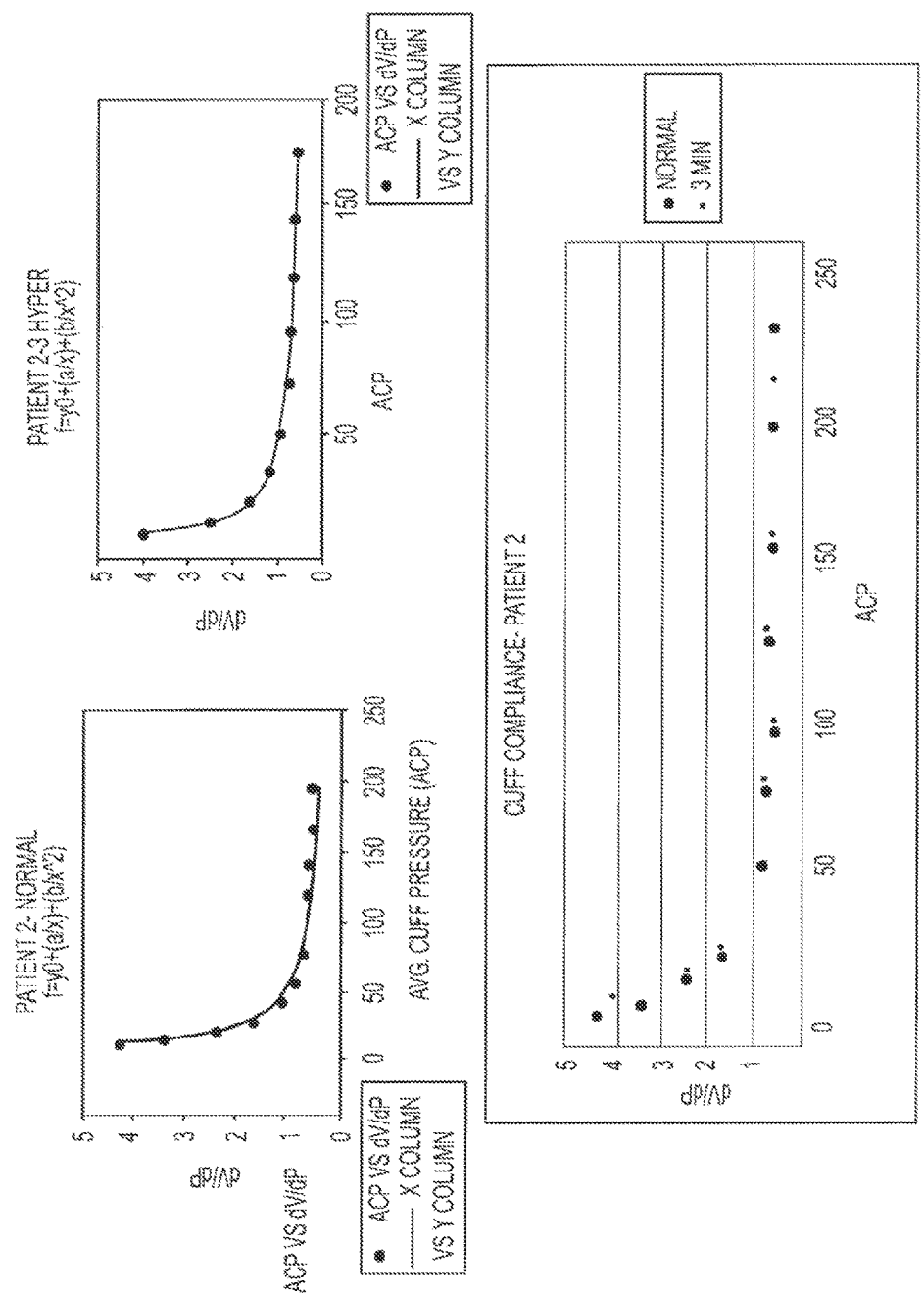

With reference to FIG. 5, shown are example cuff compliance curves generated during pressure ascent (inflation of the cuff). The cuff compliance curves may be generated as described above.

Figure 6:
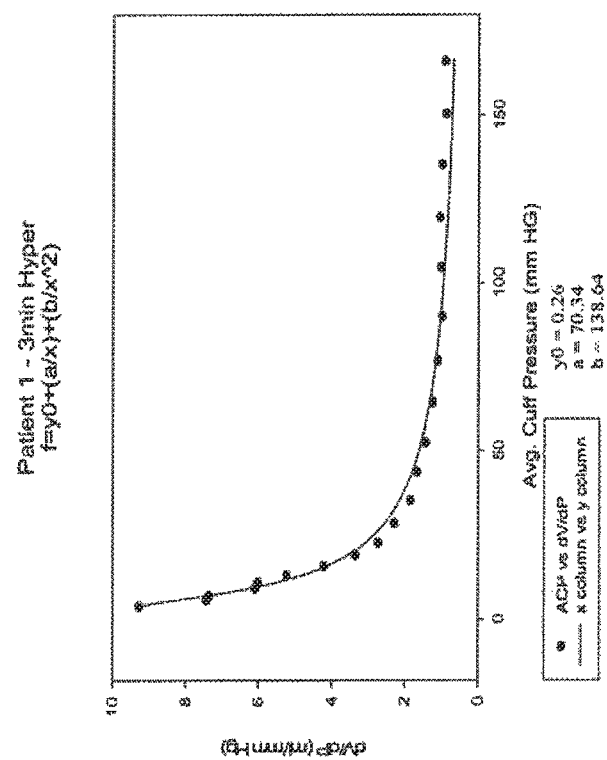
FIG. 6 is a graph illustrating cuff compliance calculated using an embodiment of the system and method for measuring arterial compliance, area and peripheral arterial flow

With reference to FIG. 6, shown is an example cuff compliance curve generated during pressure ascent using coefficients generated using non-linear regression described above. For example, inverse polynomial second order functions may be used.

The following is sample equation output where non-linear equation for cuff compliance was developed as described above. Specifically, the information below is a sample output from a non-linear regression (using an inverse polynomial second order function) performed to develop the cuff compliance curve.

Sample Output from Non-Linear Regression Used to Develop Cuff Compliance Curve
Nonlinear Regression
Equation: Polynomial, Inverse Second Order $$f = y0 + (a/x) + (b/x^2)$$

| R | Rsqr | Adj Rsqr | Standard Error of Estimate |
|---|---|---|---|
| 0.9947 | 0.9895 | 0.9883 | 0.2858 |

| | Coefficient | Std. Error | t | P | VIF |
|---|---|---|---|---|---|
| y0 | 0.2598 | 0.1091 | 2.3811 | 0.0285 | 3.0614 |
| a | 70.3371 | 3.3041 | 21.2880 | <0.0001 | 17.8907< |
| b | −138.6316 | 15.6635 | −8.8506 | <0.0001 | 12.2896< |

Analysis of Variance:
Uncorrected for the Mean of the Observations:

| | DF | SS | MS |
|---|---|---|---|
| Regression | 3 | 349.7290 | 116.5763 |
| Residual | 18 | 1.4705 | 0.0817 |
| Total | 21 | 351.1995 | 16.7238 |

Corrected for the Mean of the Observations:

| | DF | SS | MS | F | P |
|---|---|---|---|---|---|
| Regression | 2 | 138.7197 | 69.3598 | 849.0321 | <0.0001 |
| Residual | 18 | 1.4705 | 0.0817 | | |
| Total | 20 | 140.1902 | 7.0095 | | |

The resulting arterial compliance versus transmural pressure curves (arterial compliance curve) can be shown with the unit of ml/mm Hg or ml for the Y-axis, or with the unit of $cm^2$/mm Hg or $cm^2$ for the Y-axis (see FIGS. 7 and 8), which is derived by dividing the volume in ml/mm Hg or ml with the effective cuff length. In some embodiments, the final arterial compliance curves are shown with the unit of ml/mm Hg or ml for the Y-axis. In other embodiments, the final arterial compliance curves are shown with the unit of $cm^2$/mm Hg or $cm^2$ for the Y-axis.

Figure 7:
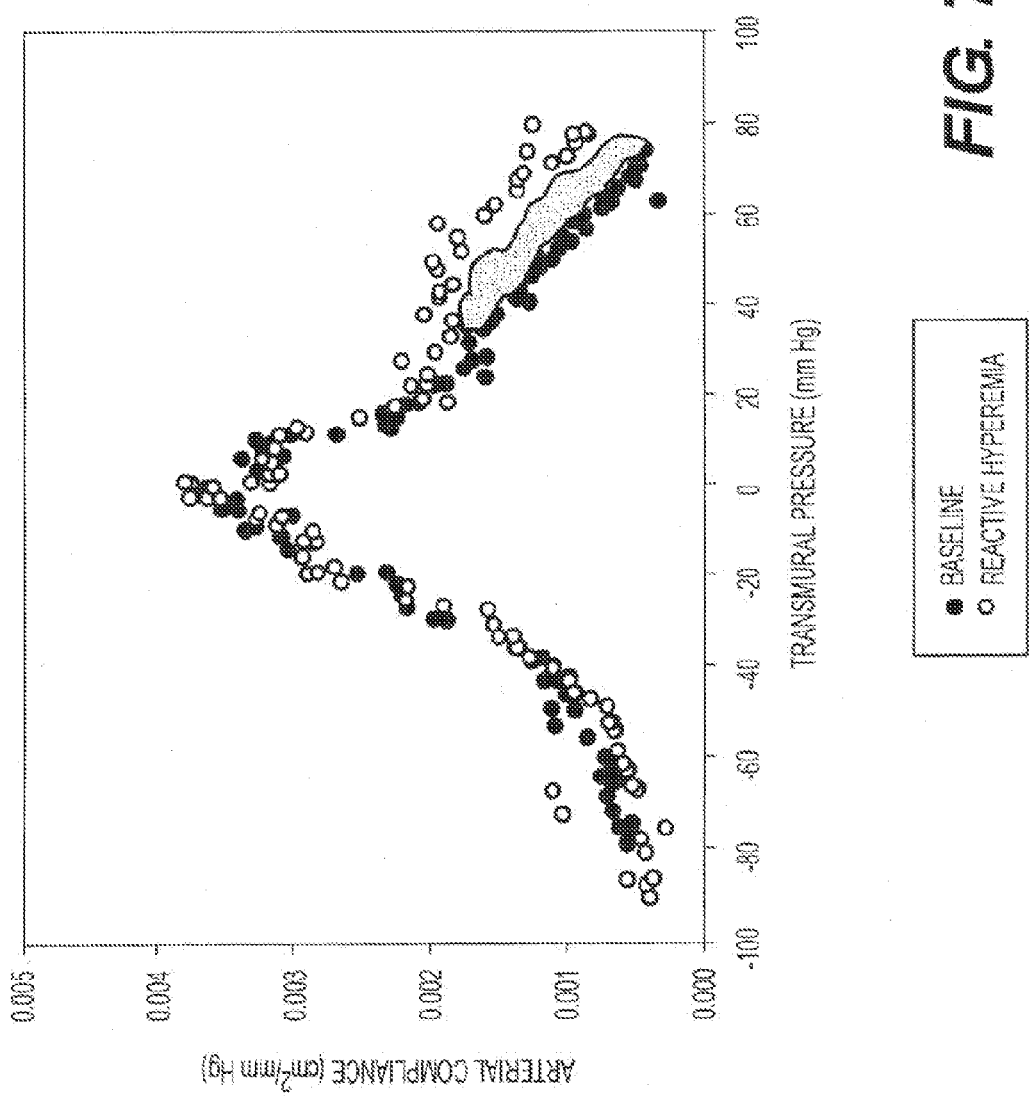
FIG. 7 is a graph illustrating a metric applied using an embodiment of the system and method for measuring arterial compliance, area and peripheral arterial flow.

The differential between normal area measurements and hyperemia measurements provides a quantitative measure of endothelial dysfunction. For example, FIG. 7 is a graph illustrating baseline and hyperemia arterial compliance curves. The differential/change between the two curves is indicated by the shaded area, which indicates the presence of endothelial dysfunction. The size of this shaded area is inversely proportional to the magnitude of endothelial dysfunction or the risk/presence of ED-related diseases (e.g., the risk/presence of pre-eclampsia).

In one embodiment, a differential percentage (i.e., the area between the baseline arterial compliance curve and the hyperemia arterial compliance curve divided by the area under the baseline arterial compliance curve) of 10% or less indicates ED or the risk/presence of an ED-related disease. In another embodiment, a differential percentage less than 7% indicates ED or the risk/presence of an ED-related disease. In another embodiment, differential percentage less than 4.5% indicates ED or the risk/presence of an ED-related disease. In summary, the lesser differential area between the baseline arterial compliance curve and the hyperemia arterial compliance curve, the greater the indication of ED or the risk/presence of an ED-related disease. In other embodiments, different thresholds are given to patient populations of different age, sex, race or geographic location In other embodiment, a scoring chart for ED based on this area, are developed in which different levels of ED correspond to different sizes of the shaded area.

In a preferred embodiment, the differential in the arterial compliance curves is determined in the portion from zero transmural pressure to the maximum transmural pressure.

In certain embodiment, a single point from a patient's normal (baseline) arterial compliance curve is compared to a single point from the patient's hyperemic arterial compliance curve at the same transmural pressure value. In a preferred embodiment, the single point comparison of the arterial compliance curves is made in the portion from zero transmural pressure to the maximum transmural pressure.

Figure 8:
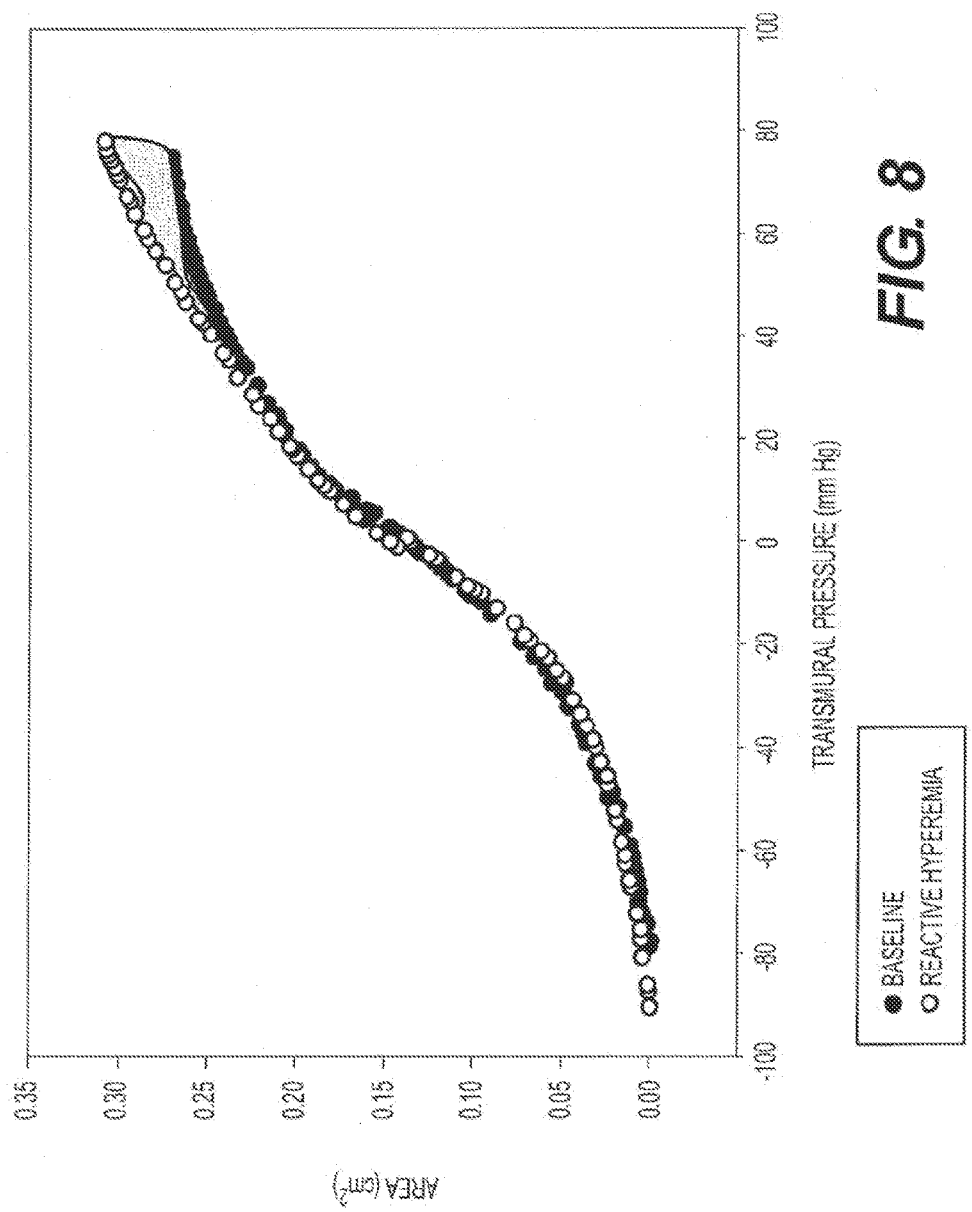
FIG. 8 is a graph illustrating a metric applied using an embodiment of the system and method for measuring arterial area.

Likewise, FIG. 8 is a graph illustrating baseline and hyperemia P-A curves. The differential/change between the two curves is indicated by the shaded area, which is inversely proportional to the presence of endothelial dysfunction. The area of this shaded area is inversely proportional to the magnitude of endothelial dysfunction or other disease (e.g., the presence of pre-eclampsia). In one embodiment, a differential percentage (i.e., the area between the baseline P-A curve and the hyperemia P-A curve divided by the area under the baseline P-A curve) of 10% or less indicates ED or the risk/presence of an ED-related disease. In another embodiment, a differential percentage less than 7% indicates ED or the risk/presence of an ED-related disease. In another embodiment, differential percentage less than 4.5% indicates ED or the risk/presence of an ED-related disease. In summary, the lesser differential area between the baseline P-A curve and the hyperemia P-A curve, the greater the indication of ED or the risk/presence of an ED-related disease. In other embodiment, different thresholds are given to patient populations of different age, sex, race or geographic location In other embodiment, a scoring chart for ED based on this area, are developed in which different levels of ED correspond to different sizes of the shaded area.

In a preferred embodiment, the differential in the P-A curves is determined in the portion from zero transmural pressure to the maximum transmural pressure.

In certain embodiment, a single point from a patient's normal (baseline) P-A curve is compared to a single point from the patient's hyperemic P-A curve at the same transmural pressure value. In a preferred embodiment, the single point comparison of the arterial compliance curves is made in the portion from zero transmural pressure to the maximum transmural pressure.

In another embodiments, the actual flow waveform at any given transmural pressure is calculated. The actual flow waveform may be calculated at any transmural pressure where blood flow is permitted by cuff pressure.

In other embodiments, the level of ED is used as an indicator for a diseased condition or as an indicator for the risk of a diseased condition. Such diseased conditions include, but are not limited to, pre-eclampsia, hypertension, atherosclerosis, cardiovascular disease (including coronary artery disease and stroke), atrial fibrillation, congestive heart failure, peripheral vascular disease, septic shock, heat stress, hypercholesterolemia, type I and II diabetes, erectile dysfunction, rheumatic arthritis, HIV, and liver disease (cirrhosis, hepatitis B and C, non-alcoholic steatohepatitis, fatty liver disease) pre-eclampsia, all forms of dementia and psychological illness, any and all illness related to localized or systemic inflammation and obesity.

In other embodiments, the pressure/volume measurements taken during the segment cuff plethysmography are used for purposes other than measuring ED. For example, the pressure/volume measurements can be used to monitor cardiac function by taking the derivative of pressure waveform and mathematically superimposing all points with the nonlinear cuff compliance relationship to generate a calibrated flow waveform.

Figure 9:
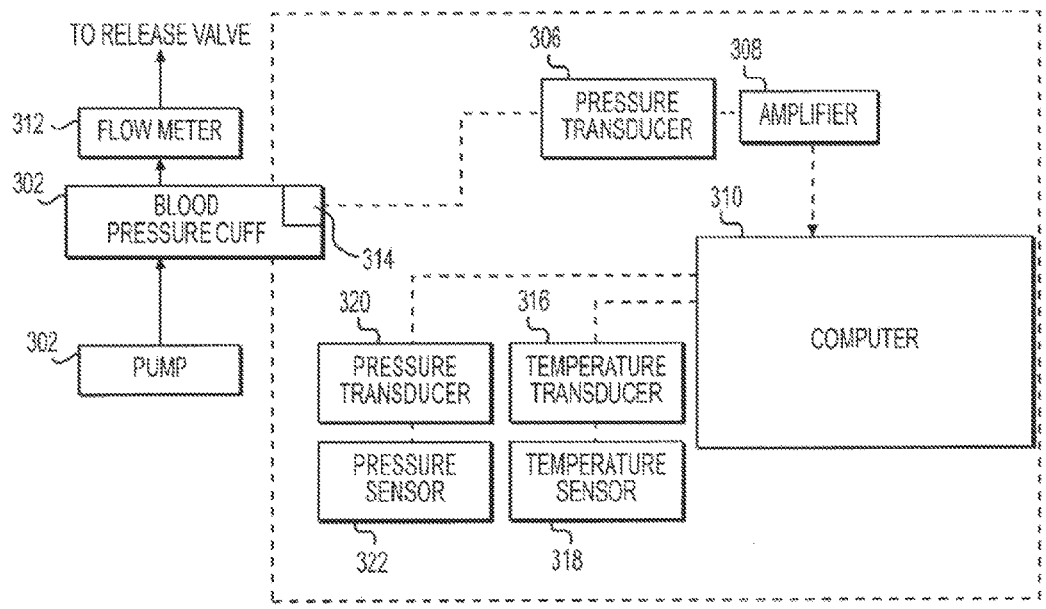
FIG. 9 is a block diagram illustrating another embodiment of a system for measuring arterial compliance, area and peripheral arterial flow.
Figure 10:
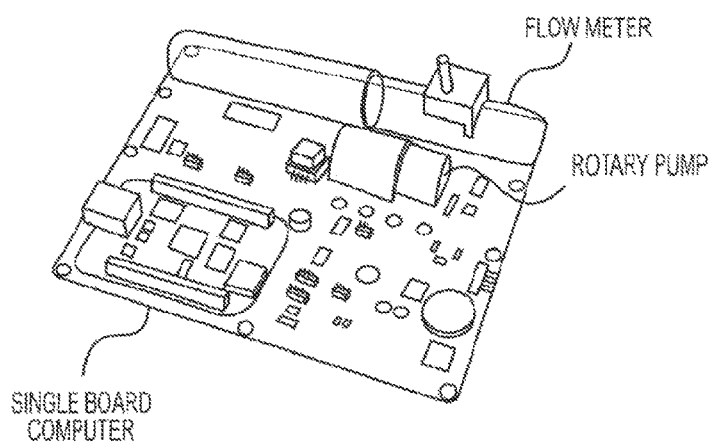
FIG. 10 is a schematic drawing of a printed circuit board (PCB) for the system of FIG. 9

With reference now to FIG. 9, shown is a block diagram illustrating another embodiment of a system 300 for measuring arterial compliance. In some embodiments, the system 300 includes a blood pressure cuff 302 having an air inlet and an air outlet, a pump 304 connected to the air inlet of the cuff 302, a pressure transducer 306, an amplifier 308, a computer 310 and a flowmeter 312 connected to the air outlet of the cuff 302. In one embodiment, the pump 304 is a rolling pump that inflates the blood pressure cuff 302 with a volume of air. In one embodiment, the pump 304 is a low frequency pump that operates at a frequency that is lower than the arterial cycle frequency. In other embodiments, the pump 304 is a low frequency pump that operates at a frequency below 10 Hertz, below 5 Hertz, below 2 Hertz, below 1 Hertz, below 0.5 Hertz, below 0.2 Hertz, below 0.1 Hertz, below 0.05 Hertz, below 0.02 Hertz, or below 0.01 Hertz. In some embodiments, the pump 304 also contains a meter to measure the volume of air injected into the cuff 302 during cuff inflation. The flowmeter 302 measures the volume of air released from the cuff 302 during cuff deflation. The pressure transducer 306 detects pulsatile pressure in the arteries of the limb by measuring the pressure in the cuff 302 through a pressure sensor 314. The pressure transducer 306 generates a signal, indicative of the pulsatile pressure that is input into the amplifier 308. Amplifier 308 amplifies the pulsatile pressure signal and inputs the amplified signal into the computer 310. In some embodiments, the system 300 further comprises a temperature sensor 318 and a pressure sensor 322 that measure the ambient temperature and pressure, respectively, as well as a temperature transducer 316 and a pressure transducer 320 that generate the ambient temperature signal and ambient pressure signal for processing at the computer 310. The purpose of the ambient pressure/temperature measurement is to provide a correction factor for volumetric measurement taking place at the flowmeter 312 using the ideal gas law principle PV=nRT With reference now to FIG. 10, shown is a schematic illustrating an embodiment of an integrated printed circuit board (PCB) 350 for the system 300. The integrated PCB 350 comprises the pump 304, the flowmeter 312, the pressure transducer 306, the amplifier 308, and the computer 310.

Figure 11:
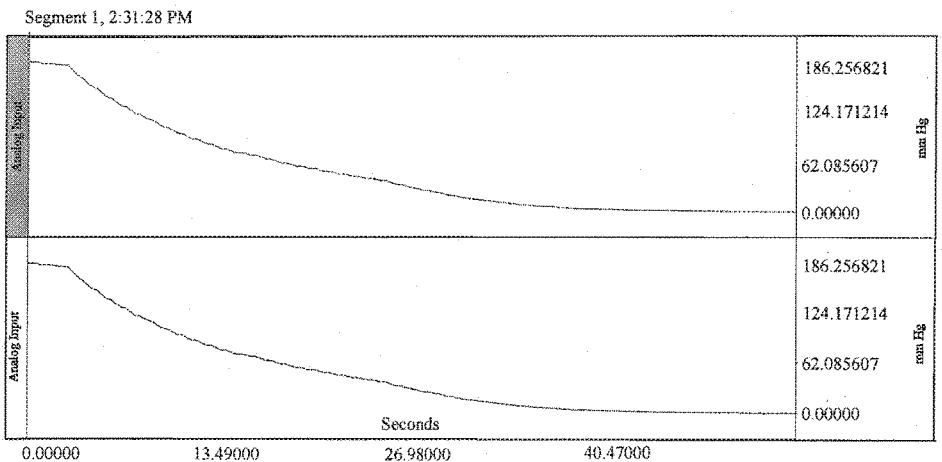
FIG. 11 shows an exemplary cuff deflation curve. During the deflation phase, the cuff pressure typically decreased from about 200 mmHg to about 0 mmHg. The patient data is typically obtained at pressure above central venous pressure which is approximately 5 mmHg

In some embodiments, all data acquisition takes place during cuff deflation and arterial compliance curve, P-V curve and P-A curve are all generated based only on data collected during the cuff deflation phase. FIG. 11 shows an exemplary cuff deflation curve. During the deflation phase, the cuff pressure decreased from about 200 mmHg to about 0 mmHg. The following information is obtained i. Mean Cuff Pressure (MCP)
ii. decremental Volume Change (dV)
iii. decremental Pressure Change (dP)

The volumetric decrements (dV) is directly measured by the flowmeter 312. The decremental pressure change (dP) corresponding with each volumetric decrement (dV) is also directly measured by the pressure transducer 306 through the pressure sensor 314 on the cuff 302. The Cuff compliance (CC) is calculated for each MCP.

$$CC=(dV/dP)_{cuff}$$

Figure 12:
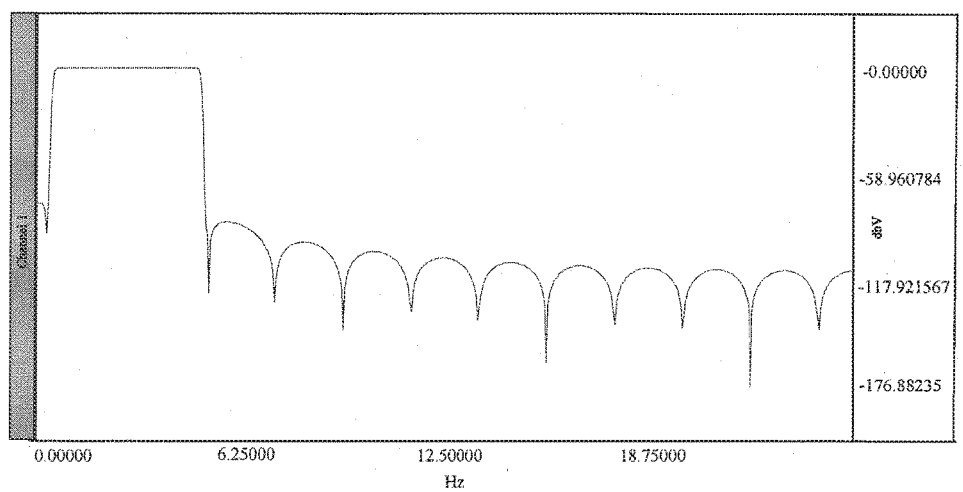
FIG. 12 shows an exemplary band pass filter frequency response output.
Figure 13:
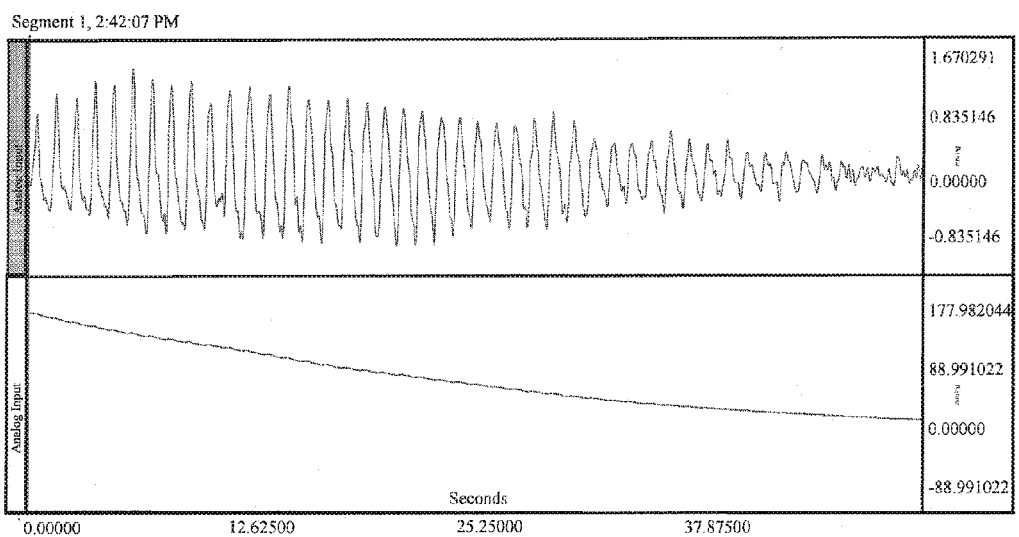
FIG. 13 shows band pass filter (0.5-5.0 Hertz) of cuff descent data (top panel) and standard cuff descent data (bottom panel).

A cuff compliance curve is then generated based on measured pressure change for each measured volume change obtained during the deflation. During deflation, the actual volume measurements provide increased accuracy in the formulation of the cuff compliance values as the pressure descends at all cuff pressures. This leads to increased accuracy of the arterial compliance term. The benefit in this accuracy is that clinicians now have temporal data that allows them to compare measurement over any time period Next, a band pass filter (0.5-5.0 Hertz) is applied to the cuff pressure curve data. FIG. 12 shows an exemplary band pass filter frequency response output. FIG. 13 shows band pass filter (0.5-5.0 Hertz) of cuff descent data (top panel) and standard cuff descent data (bottom panel). In one embodiment, an additional DC low pass filter (0-0.5 Hz) is used to obtain the flowrate as air leaves the cuff. This is used to obtain the actual volume changes. The mean arterial pressure (MAP), Systolic Blood Pressure (SBP) and Diastolic Blood Pressure (DBP) are calculated using the following rules:

(a) MAP corresponds with the largest peak-to-peak measurement. Record the magnitude;
(b) SBP corresponds with approximately 55% of the magnitude of the largest peak-to-peak measurement. Find the peak-to-peak value that corresponds most closely with this value (at a cuff pressure greater than MAP) and find the cuff pressure. This cuff pressure is equivalent to SBP; and
(c) DBP corresponds with approximately 85% of the magnitude of the largest peak-to-peak measurement. Find the peak-to-peak value that corresponds most closely with this value (at a cuff pressure less than MAP) and find the cuff pressure. This cuff pressure is equivalent to DBP.

The arterial compliance curve ($(dV/dP)_{artery}$ v. transmural pressure) is then generated via the following calculation:

$$(dV/dP)_{artery}=[(dV/dP)_{cuff} \times dP_{cuff}]/dP_{artery} \qquad \text{i.}$$

$$dP_{artery}=SBP-DBP \qquad \text{ii.}$$

$$\text{Transmural pressure}=MAP-\text{Cuff Pressure.} \qquad \text{iii.}$$

A pressure-volume (P-V) curve and pressure-area (P-A) curve can be generated via integration of the arterial compliance curve (designated as baseline arterial compliance, P-V and P-A curves). The procedure is then repeated during the second segmental plethysmography, where the cuff pressure is held for a period of 1-10 minutes, 2-8 minutes, 2-5 minutes or about 5 minutes, to produce the arterial compliance, pressure-volume (P-V) and pressure-area (P-A) curves (designated as hyperemia arterial compliance, P-V and P-A curves). In some embodiments, the area between the baseline and hyperemia arterial compliance curves is calculated and used for the evaluation of ED. In some embodiments, only the area that is within the transmural pressure range of 0-120 mmHg, 0-100 mmHg, 0-80 mmHg, 20-120 mmHg, 20-100 mmHg, or 20-80 mmHg is calculated.

In some embodiments, the area between the baseline and hyperemia P-A curves is calculated and used for the evaluation of ED. In some embodiments, only the area that is within the transmural pressure range of 0-120 mmHg, 0-100 mmHg, 0-80 mmHg, 20-120 mmHg, 20-100 mmHg, or 20-80 mmHg is calculated.

The embodiments described herein enable a physician, for example, to both measure and monitor reactive hyperemia, ED, ED-related diseases, cardiovascular conditions and the efficacy of various forms of treatment. Key metrics obtained include actual measurements of peripheral arterial flow, arterial compliance, and arterial area across the entire arterial transmural pressure range.

A significant benefit of the embodiments described herein is the early diagnosis of ED-related diseases. A physician, for example, is able to gain valuable information from the reactive hyperemic measurement. Device embodiments provide benefits to clinicians in providing a simple method to diagnose patients that are currently classified as asymptomatic, as well as quantify the efficacy of current and novel treatments in patients already diagnosed with disease. Another significant benefit of the embodiments described herein is the ability to monitor the effectiveness of treatments for ED The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A method for determining a risk of an endothelial dysfunction (ED)-related disease in a subject, comprising:
   performing a first segmental cuff plethysmography having an inflation phase and a deflation phase and generating a first cuff compliance curve based only on data collected during the deflation phase of the first segmental cuff plethysmography;
   generating a baseline arterial compliance curve and/or a baseline pressure-area (P-A) curve on a portion of the body of the subject, wherein the cuff pressure is increased to a first peak cuff pressure during the inflation phase and immediately reduced from the first peak cuff pressure during the deflation phase;
   performing a second segmental cuff plethysmography having an inflation phase, a holding phase, and a deflation phase and generating a second cuff compliance curve based only on data collected during the deflation phase of the first segmental cuff plethysmography;
   generating a hyperemic arterial compliance curve and/or a hyperemic P-A curve, wherein the cuff pressure is increased to a second peak level during the inflation phase, maintained at the second peak cuff pressure for a predetermined period of time during the holding phase, and then reduced from the second peak cuff pressure during the deflation phase;
   calculating the difference between the baseline arterial compliance curve and the hyperemic arterial compliance curve as an area between the arterial compliance curves, and/or the difference between the baseline P-A curve and the hyperemic P-A curve as an area between the P-A curves;
   measuring a level of reactive hyperemia based on the area between the arterial compliance curves and/or the area between the P-A curves; and
   determining a risk of an ED-related disease based on the result of the measuring step, wherein the first and second cuff compliance curves are generated using a flowmeter that directly measures a volume change in the cuff during the deflation phase, and
   wherein the ED-related disease is selected from the group consisting of coronary artery disease, heat stress, cirrhosis, hepatitis B and C, non-alcoholic steatohepatitis, fatty liver disease, all forms of dementia and psychological illness, and all illness related to localized or systemic inflammation and obesity.

2. The method of claim 1, wherein said cuff is inflated during the first and second segmental cuff plethysmography using a low-frequency pump.

3. The method of claim 2, wherein said low-frequency pump has an operation frequency of 10 Hertz or lower.

4. The method of claim 2, wherein said low-frequency pump has an operation frequency of 2 Hertz or lower.

5. The method of claim 1, further comprising:
   determining a level of endothelial dysfunction (ED) in the subject based on the result of the measuring step.

6. The method of claim 1, wherein the first peak cuff pressure and the second peak cuff pressure are in the range of 150-180 mmHg.

7. The method of claim 1, wherein the predetermined period of time is about 2-10 minutes.

8. The method of claim 1, wherein the calculating step calculates the difference between the baseline arterial compliance curve and the hyperemic arterial compliance curve as an area between the arterial compliance curves within a transmural pressure range of 0-100 mmHg, and wherein the calculating step calculates the difference between the baseline P-A curve and the hyperemic P-A curve as an area between the P-A curves within a transmural pressure range of 0-100 mmHg.

9. The method of claim 8, wherein the calculating step calculates the difference between the baseline arterial compliance curve and the hyperemic arterial compliance curve as an area between the arterial compliance curves within a transmural pressure range of 20-80 mmHg, and wherein the calculating step calculates the difference between the baseline P-A curve and the hyperemic P-A curve as an area between the P-A curves within a transmural pressure range of 20-80 mmHg.

10. The method of claim 1, wherein the generation of said baseline arterial compliance curve and/or a baseline pressure-area (P-A) curve comprises applying a band pass filter of 0.5-5.0 Hertz to cuff pressure data collected during the deflation phase of said first segmental cuff plethysmography and wherein the generation of said hyperemia arterial compliance curve and/or hyperemia pressure-area (P-A) curve comprising applying a band pass filter of 0.5-5.0 Hertz to cuff pressure data collected during the deflation phase of said second segmental cuff plethysmography.

11. The method of claim 10, wherein an additional DC low pass filter between 0 Hz and 0.5 Hz is used to generate flowrate data during the deflation phase of said first and second segmental cuff plethysmography.

12. The method of claim 1, wherein the ED-related disease is coronary artery disease or heat stress.

13. The method of claim 1, wherein the ED-related disease is cirrhosis, hepatitis B, hepatitis C, non-alcoholic steatohepatitis or fatty liver disease.

14. The method of claim 1, wherein the ED-related disease is dementia.

15. The method of claim 1, wherein the ED-related disease is a psychological illness.

16. The method of claim 1, wherein the ED-related disease is an illness related to localized inflammation.

17. The method of claim 1, wherein the ED-related disease is an illness related to systemic inflammation.

18. The method of claim 1, wherein the ED-related disease is an illness related to obesity.

* * * * *